United States Patent [19]

Kemp et al.

[11] Patent Number: 5,378,469
[45] Date of Patent: Jan. 3, 1995

[54] COLLAGEN THREADS

[75] Inventors: Paul D. Kemp, Winchester; Robert M. Carr, Jr., Boston; John G. Maresh, Somerville; John Cavallaro, Gloucester; Jerome Gross, Waban, all of Mass.

[73] Assignee: Organogenesis, Inc., Canton, Mass.

[21] Appl. No.: 772,529

[22] Filed: Oct. 7, 1991

Related U.S. Application Data

[63] Continuation-in-part of Ser. No. 505,678, Apr. 6, 1990, Pat. No. 5,256,418.

[51] Int. Cl.[6] .......................... A61F 2/28; A61K 9/14; A61K 37/12; C07K 15/20
[52] U.S. Cl. .................................. 424/423; 424/426; 424/484; 623/11; 623/12; 623/16; 623/901; 264/178 R
[58] Field of Search ............... 424/422, 423, 424, 425, 424/426, 456, 486, 484, 485, 491, 492; 514/2, 801, 944, 12, 774; 530/356, 840, 353, 355; 128/65; 623/11, 12, 16, 901; 264/178 R

[56] References Cited

U.S. PATENT DOCUMENTS

| | | | |
|---|---|---|---|
| 3,644,202 | 2/1972 | Higley | 210/653 |
| 4,863,732 | 9/1989 | Nathan et al. | 514/801 |
| 4,980,403 | 12/1990 | Bateman et al. | 530/350 |
| 5,256,418 | 10/1993 | Kemp et al. | 424/423 |

FOREIGN PATENT DOCUMENTS

| | | |
|---|---|---|
| 0083868 | 12/1982 | European Pat. Off. |
| 0243132 | 4/1987 | European Pat. Off. |
| 0268421 | 11/1987 | European Pat. Off. |
| WO88/08305 | 11/1988 | WIPO |

Primary Examiner—G. S. Kishore
Assistant Examiner—C. Azpuru
Attorney, Agent, or Firm—David G. Conlin; Linda M. Buckley

[57] ABSTRACT

The present invention provides improved collagen threads and methods of making and using such threads, including the production of yarn, as well as braided, knitted, and woven articles of manufacture, comprising such threads.

12 Claims, 1 Drawing Sheet

COLLAGEN THREADS

BACKGROUND OF THE INVENTION

This application is a continuation-in-part of U.S. application Ser. No. 07/505,678, filed Apr. 6, 1990, which is now U.S. Pat. No. 5,256,418, the disclosure of which is incorporated herein by reference.

This invention relates to improved collagen threads, to methods for the production of such collagen threads, and to articles of manufacture incorporating such threads, for example, knitted and woven articles.

Collagen is usually found as the principal protein component of the extra-cellular matrix, and in mammals collagen sometimes constitutes as much as 60% of the total body protein. For example, it comprises most of the organic matter of skin, tendons, bones and teeth, and occurs as fibrous inclusions in most other body structures. Collagen is a relatively weak immunogen, due in part to masking of potential antigenic determinants by the helical structure. This helical structure also makes collagen resistant to proteolysis. Furthermore, collagen is a natural substance for cell adhesion and is the major tensile load-bearing component of the musculo-skeletal system.

Because of the foregoing properties, collagen has diverse applications in the medical products area, such as in the manufacture of implantable prostheses, as cell growth substrates, and in the preparation of living tissue equivalents. Indeed, much work has been done to develop collagen products for such applications, including products for use in research and developnent, tissue and organ repairland/or replacement. Methods for producing collagen threads for such applications are known in the art.

U.S. Pat. No. 3,114,593 disclosed the production of collagen strands by extruding swollen collagen fibrils to form a multifilament and applying a water-miscible organic liquid dehydrating agent more volatile than water to the multifilament, and stretching and twisting the multifilament while evaporating the organic liquid so that the multifilament unites to from a strand. The swollen collagen fibrils were extruded from a collagen solution at 0.73 to 0.82% by weight (7.3 to 8.2 mg/ml). Yet other methods are disclosed in U.S. Pat. Nos. 2,598,608, and 2,637,321 wherein extrusion is carried out with collagen dispersions on the order of 2–15% by weight (20 to 150 mg/ml) collagen.

Methods of forming collagen fibers are also disclosed in Kato and Silver, *Biomaterials*, 11 (1990) 169–175. In this method collagen is first extruded into an aqueous fiber formation bath, wherein the collagen is neutralized and a weak collagen fiber formed. This low tensile strength fiber is then carried via a conveyor belt through alcohol and water baths. One disadvantagage in this method is that fibrils are formed from a relatively dilute collagen solution resulting in a thread so weak that it must be carried on a conveyor belt through the dehydrating bath.

Improved collagen threads or fibers and methods of producing the same are being sought.

SUMMARY OF THE INVENTION

Figure 1:
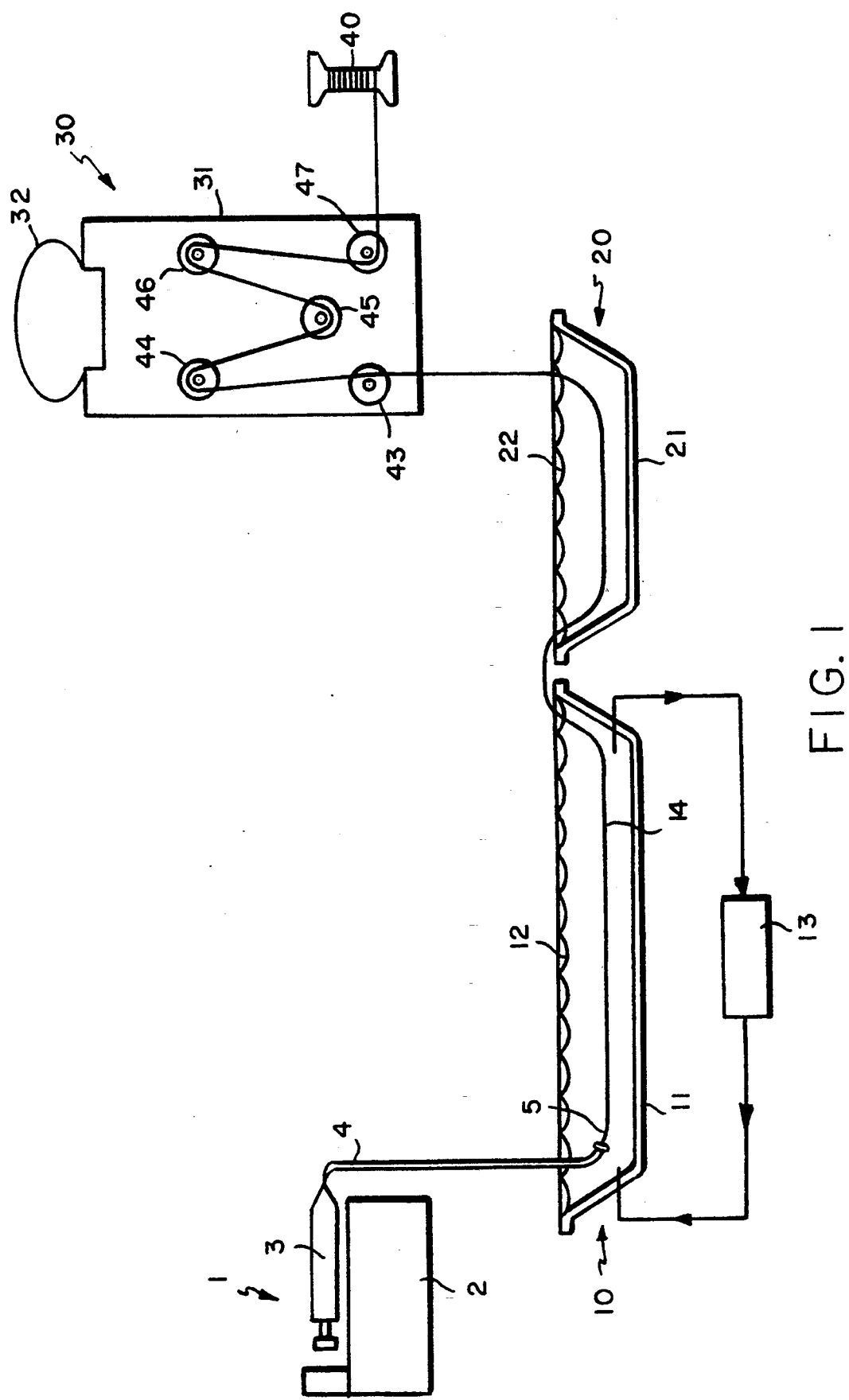
FIG. 1 is a schematic representation of one apparatus for use in the methods of the present invention.

This invention provides collagen threads, including collagen threads suitable for knitting and weaving, articles of manufacture comprising such threads, including tissue constructs, and methods of making and using such threads.

The present invention provides collagen threads having improved properties over known collagen threads. Preferred collagen threads in accordance with the present invention have an ultimate tensile strength of greater than about 1 for noncrosslinked threads and greater than about 45 for crosslinked threads. One particularly preferred thread of the present invention has the following properties:

|  | Non XL | Glut XL |
| --- | --- | --- |
| Ultimate tensile strength | 1.7 ± 0.6 | 70 ± 7.0 |
| Ultimate strain (%) | 30 ± 10 | 45 ± 10 |
| Modulus (MPa) | 5.7 ± 2.0 | 134 ± 13 |
| Load at Break | 11 ± 3.9 | 167 ± 9.6 |
| Swelling (%) | 390 ± 35 | 63 ± 9.1 |

The present invention also provides methods of making thread comprising collagen, wherein a solution comprising collagen is extruded into a dehydrating agent which has a higher osmotic pressure than that of the collagen solution and a pH from about 5 to about 9. The dehydrating agent is maintained under conditions to enable the discharged collagen to form a thread. A preferred dehydrating agent comprises polyethylene glycol (PEG) or DEXTRAN ® in a phosphate or borate buffer. About 20 to 35% by weight of PEG has been found particularly useful.

Some preferred methods of the present invention further comprise a rinsing step to provide additional flexibility to the collagen thread. One preferred rinsing bath comprises phosphate buffered saline.

The present invention also provides banded collagen threads are provided. Such banded threads appear to be very similar to native-banded collagen fibrils.

DETAILED DESCRIPTION OF THE INVENTION

In one preferred method of the present invention, collagen threads are made by a method comprising:
(a) extruding a solution comprising collagen into a dehydrating agent, the dehydrating agent having a higher osmotic pressure than that of the collagen solution and a pH from about 5 to 9; and
(b) maintaining the dehydrating agent under conditions to enable collagen thread formation.

In other preferred methods of the present invention, the method of making collagen threads further comprises rinsing the formed thread in a buffer to provide additional flexibility. This optional step is particularly useful in applications wherein the collagen thread will be knitted or woven.

In some instances, it is desirable to crosslink the collagen thread in order to improve its strength, particularly its wet strength. Accordingly, in yet other preferred embodiments of the present invention, the collagen thread is crosslinked. Although crosslinking may be carried out without rinsing the thread, in particularly preferred embodiments the thread is rinsed and dried before crosslinking is carried out.

In yet other preferred methods of the present invention, banded collagen threads are produced, at least in part, by selecting the appropriate dehydrating agent system.

Collagen for use in the present invention may be obtained from any suitable source. Typical sources include skin and tendons. Many procedures for obtaining and purifying collagen, typically involving acid or enzyme extraction, are known to practitioners in the art and may be used to prepare collagen for use in the present invention. A preferred collagen composition for use herein is obtained from a novel source, the bovine common digital extensor tendon, and by a novel extraction method, both as disclosed in copending U.S. patent application Ser. No. 07/407,465, filed Sep. 15, 1989, the disclosure of which is incorporated herein by reference. Although both monomers and mixtures of monomers and higher ordered collagen polymers, e.g., dimers up to and including fibrils, can be used in the practice of the present invention, monomers are preferred for many applications.

Collagen solutions for use in the present invention are generally at a concentration of about 2 to 10 mg/ml, preferably, from about 4 to 6 mg/ml, and most preferably at about 4.5 to 5.5 mg/ml and at pH of about 2 to 4. A preferred solvent for the collagen is dilute acetic acid, e.g., about 0.05 to 0.1%. Other conventional solvents for collagen may be used as long as such solvents are compatible with thread formation and the desired properties of the collagen thread. These collagen solutions may contain optional components known to those of ordinary skill in the art, such as neutral and charged polymers, including but not limited to, polyvinyl alcohol and hyaluronic acid.

The collagen solution is preferably degassed or debubbled before extrusion into a dehydrating bath. This may be accomplished, for example, by centrifugation, as well as other methods well known to practitioners in the art.

The dehydrating bath comprises a dehydrating agent having a higher osmotic pressure than that of the collagen solution, preferably higher than about 500 mOsm, and a pH from about 5 to 10, with a pH of about 7 to 9 being preferred. Preferred dehydrating agents include water soluble, biocompatible polymers such as DEXTRAN ® and polyethylene glycol (PEG). In preferred embodiments, the dehydrating agent is dissolved in a buffer such as sodium phosphate or sodium borate. One preferred dehydrating bath for use in the methods of the present invention comprises about 20 to 30% by weight PEG in phosphate buffer.

Native-banded collagen fibrils are typically formed within the collagen threads, when the dehydrating bath comprises sodium phosphate at 0.1 to 0.5M. It has been found that borate buffer inhibits the formation of native-banded fibrils. While not wishing to be bound by theory, it is believed that borate may inhibit band formation by binding to the collagen.

In embodiments wherein it is desired to impart additional flexibility to the thread, e.g., where the thread is to be knitted or woven, the collagen thread may be rinsed. A preferred rinsing bath for use in the present invention comprises phosphate buffered saline ("PBS") having a phosphate concentration of about 0.001 to 0.02M and a NaCl concentration of about 0.05 to 0.1M. In a particularly preferred embodiment, a phosphate buffered saline solution is prepared as described hereinafter in Example I. The pH of the rinsing bath is kept above a pH of about 5, to prevent the thread from over hydrating. A preferred pH range is from about 6 to about 8.

In another preferred embodiment of the present invention, the collagen thread is crosslinked to increase the strength, e.g., the wet tensile strength, of the thread. This can be accomplished by any number of methods known to those of ordinary skill in the art, including lyophilization, u.v. irradiation, or contact with an aldehyde such as glutaraldehyde. Carbodiimides such as 1-ethyl-3-(3-dimethylaminopropyl) carbodiimide hydrochloride (EDC) have also been used to crosslink collagen thread, but such crosslinking occurs at a slower rate than with glutaraldehyde.

For the purposes of description only, the methods of the present invention will be illustrated by preparing collagen threads by means of the apparatus shown in FIG. 1. It will be understood to those skilled in the art that the methods of the present invention are not limited to the apparatus shown.

Referring to FIG. 1, there is shown a schematic diagram of one form of an apparatus which may be used for producing collagen threads in accordance with the present invention. As shown in FIG. 1, the apparatus comprises means for extruding the collagen solution 1, dehydrating bath 10, rinsing bath means for drying the collagen thread 30, and means for collecting the collagen thread which includes uptake spool 40 and a driver, not shown, for the uptake spool 40.

As shown in FIG. 1, means 1 for extruding a collagen solution includes a syringe pump 2, a syringe 3, leader tubing 4, and a blunt needle 51. The dehydrating bath 10, includes dehydrating trough 11, dehydrating agent 12 and recirculating pump 13. The rinsing bath 20 includes a rinsing trough 21 and rinse liquid 22. The means for drying the collagen thread 30 includes a drying cabinet 31, pulleys 43 to 47, and a heated blower 32. The thread is carried through and out of the apparatus by means of a series of pulleys 43 to 47 and uptake spool 40, driven by an uptake driver, not shown.

In one preferred embodiment, a solution of collagen at 5 mg/ml in 0.05% acetic acid is degassed, loaded into the syringe 3, and connected to the leader tubing 4 and needle 5. The syringe 3 is placed in position relative to syringe pump 2 so that the pump 2 can act on the syringe 3 to extrude the collagen solution. The leader tubing 4 and needle 5 are placed in the dehydrating bath 11 under the surface of dehydrating agent 12. Although a syringe pump and syringe are used to illustrate the extrusion of collagen in accordance with the present invention, those of ordinary skill in the art of polymer extrusion will recognize that extrusion can also be carried out by use of other conventional devices.

Preferred materials for the apparatus described are compatible with thread formation, the desired properties of the thread and the materials used in thread formation, e.g., acetic acid at about 3 pH. In some instances the apparatus must be capable of sterilization.

The thickness of the extruded collagen thread is determined in part both by the rate of infusion of the collagen solution into the dehydration bath and flow rate of the dehydrating agent in the trough 11. The syringe pump 2 is set to extrude the collagen solution at a rate which is typically between about 2.0 to 3.5 ml/min., depending upon the collagen solution. Dehydration trough 11 is configured to provide sufficient capacity for the desired volume of dehydrating agent 12. Dehydration trough 11 is constructed of a material which is compatible with collagen and the reagents used. Such materials include PVC and polycarbonate. The dehydration trough 11 is provided with a recirculating pump 13 to recirculate the dehydrating agent 12. The rate of extrusion of the collagen solution and the rate of circulation of the dehydrating agent 12 and the length of trough 11 are selected to provide the desired minimum residence time in the dehydrating agent 12.

The flow of the circulating dehydrating agent 12 draws the thread. When a collagen thread 14 of sufficient length has been formed, the leading end of the thread is removed from the dehydration trough 11, and transferred into the rinsing trough 21.

When enough slack is generated, the thread is moved through the rinsing trough 21, disposed pulley 43 of the drying cabinet 30. A heated blower 32 is activated and the collagen thread is disposed on pulleys 44 to 47 and eventually on uptake spool 40. The drying temperature in the chamber is typically about 30° C. to 45° C., more preferably 43° C. The speed of uptake spool 40 is controlled by an uptake driver, not shown, and adjusted so that the thread emerges dry to the touch from drying cabinet 30.

In some preferred embodiments, the collagen thread is crosslinked to increase its wet tensile strength. In one particularly preferred embodiment, the thread is removed from the uptake spool 40 after drying and then crosslinked by pulling the thread through a solution of 2% glutaraldehyde. By way of comparison, the wet strength of uncrosslinked collagen threads in accordance with the present invention has been found to be about 5-25 g, whereas the wet strength of crosslinked thread was about 50-150 g. If the thread is not crosslinked, it has been found that the wet strength is generally about 1-10% of the dry strength, whereas if the thread is crosslinked, the wet strength is about 60 to 100% of the dry strength.

The collagen threads prepared in accordance with the present invention may have a collagen concentration of about 300 to 600 mg/ml.

When collagen produced by the methods of U.S. Ser. No. 07/407,465, supra., is used to prepare threads in accordance with the present invention, superior threads are obtained as compared to use of, e.g., commercially available pepsin extracted collagen (Pentapharm). For example, a collagen thread prepared in accordance with the present invention from such pepsin extracted collagen had a wet strength of only 2 g, whereas thread produced using collagen of U.S. Ser. No. 07/407,465 had a wet strength of 15 g.

The methods of the present invention have been used to produce collagen threads of about 50 μm to 250 μm in diameter. However, threads having diameters outside this range can be produced if desired for certain applications. Typical physical properties of threads produced in accordance with the methods of the present invention are given in Table I below:

TABLE I

| Denier | 75-90 |
| --- | --- |
| Dry Strength (y) | 220 |
| Elongation at break | 20 |
| Tenacity | 2-3 |
| % Moisture | 30 |
| Wet strength uncrosslinked (g) | 15 |
| crosslinked (g) | 180 |

Collagen produced in accordance with U.S. Ser. No. 07/407,465 was used to produce collagen threads in accordance with the present invention (Thread B). In Table II below, typical properties of Thread B determined using standard methodolgies are compared with the reported properties of threads produced in Kato and Singer, supra. (See page 171, Table 1). (Thread A). Thread B was soaked in PBS in accordance with the teachings of Kato and Singer.

TABLE II

MECHANICAL PROPERTIES OF CONTINUOUS COLLAGEN THREADS AFTER SOAKING IN PBS

|  | Thread A | | Thread B | |
| --- | --- | --- | --- | --- |
|  | Non XL | Glut XL | Non XL | Glut XL |
| Ultimate tensile strength (MPa) | 0.8 ± 0.2 | 37 ± 7.9 | 1.7 ± 0.6 | 70 ± 7.0 |
| Ultimate strain (%) | 38 ± 4.9 | 17 ± 3.0 | 30 ± 10 | 45 ± 10 |
| Modulus (MPa) | 3.6 ± 0.8 | 270 ± 69 | 5.7 ± 2.0 | 134 ± 13 |
| Load at Break (gm) | 1.2 ± 0.3 | 14 ± 2.5 | 11 ± 3.9 | 167 ± 9.6 |
| Swelling (%) | 165 ± 16 | 24 ± 9.9 | 390 ± 35 | 63 ± 9.1 |

It can be seen that the collagen threads of the present invention have superior properties.

The threads of the present invention have numerous applications and can serve, e.g., as the support scaffold for living tissue equivalents, such as, blood vessels or tendon prosthesis. Constructs formed from such threads provide, e.g., suitable surfaces for cell growth.

Constructs may be formed from the collagen threads of the present invention by techniques for processing fibers know to those skilled in the art, e.g., knitting and weaving. Most fiber handling techniques for both natural fibers, e.g., cotton, silk, etc., and synthetic fibers, e.g., nylon, cellulose acetate, etc., should be useful in processing threads provided herein, including techniques used to produce three-dimensional textiles. See, e.g., Mohamed, *American Scientist*, 78 (1990) 530-541.

Collagen threads provided by the present invention have been used to form braided constructs (See Example 3 below), plied into yarn (See Example 4 below), and knitted (See Example 5 below). It is expected that the collagen threads of the present invention can also be successfully woven using techniques known to the skilled artisan to produce woven contstruct. In such applications, the numbers of collagen threads used, as well as the combination of cross-linked ("XL") and uncross-linked threads, can be varied as desired.

A knitted tube comprising two ply yarn, a twist of one XL and one non-XL collagen thread of the present invention, has been used in the preparation of a blood vessel construct as described in Example 6 below.

The invention will be further understood with respect to the following examples which are purely exemplary in nature and are not meant to be utilized to limit the scope of the invention.

An apparatus similar to that shown in FIG. 1 was used in carrying out the work described in the following examples.

The baths described below were used in the following examples unless otherwise noted:

A. Dehydrating Bath 1200 g PEG (8000), 20 g of monobasic sodium phosphate (monohydrate) and 71.6 g of dibasic sodium phosphate (anhydrous) were dissolved approximately 4000 ml water in the 10 L vessel and mixed well until the solids were dissolved. The pH was then adjusted to 7.50±0.05 with 1N NaOH and water added to a final volume of 6000 ml.

B. Rinse Bath

Phosphate Buffered Saline (PBS) was prepared by dissolving 0.35 g Potassium phosphate monobasic, 7.5 g Sodium phosphate dibasic heptahydrate, and 22.5 g Sodium Chloride in water and adjusting the find volume to 5000 ml.

EXAMPLE 1—COLLAGEN THREAD PRODUCTION

A. Materials and Equipment

1. Collagen: Collagen was prepared as disclosed in U.S. Ser. No. 07/407,465, supra, and stored at 4° C. until ready to use. Collagen in 0.05% acetic acid at 5.0 mg/ml was degassed by centrifugation prior to use.
2. Beckton Dickinson 60 cc syringe with widely spaced O-rings.
3. Popper & Sons, Inc. blunt stainless steel needle, 18 gauge, with silicone leader tubing and bridge.
4. Harvard Apparatus Syringe Pump (Pump 22).
5. An 18 foot long PVC dehydration trough 2 inches in diameter, with Masterflex Pump and norprene tubing.
6. Dehydrating Agent 20: PEG (8000 M. Wt.) from Spectrum, phosphate-buffered at approximately pH 7.50.
7. A rinsing trough, 6 feet in length.
8. Rinsing bath (½×PBS).
9. Drying cabinet with pulleys and heated blowers (2).
10. Level wind uptake spool and driver.

B. Extrusion

Approximately 6000 ml of dehydrating agent was poured into the dehydrating trough and the recirculating pump was started. The dehydration agent velocity was about 5 cm/sec for collagen solutions having viscosities of about 400 $cs^{-1}$.

Approximately 4000 ml of the rinsing bath (½×PBS) was added to the rinsing trough.

A needle was placed into the dehydrating agent approximately 12 inches from the upstream end. The collagen syringe barrel was attached to the syringe pump, the pump set to at an infusion rate of about 2.5 ml/min., and the infusion pump started.

When enough slack was generated in the dehydration trough, the thread was manually transferred through the rinsing trough and disposed over the first pulley in the drying cabinet. The thread typically sat for about 3 minutes in the rinsing trough. The heated blower was then turned on set to "low." i.e., about 30°-45° C. Gradually, as the thread dried, the collagen thread was then carefully disposed over the pulleys in a zig-zag fashion.

The free end of the thread was wound onto the uptake spool. The speed of the uptake spool was set so that the thread emerged dry to the touch from the cabinet.

Continuous thread of up to 75 meters has been produced.

EXAMPLE 2—CROSSLINKING COLLAGEN THREAD

The collagen thread was drawn through a 6 inch polycarbonate trough containing 2.0% paraformaldehyde, 2.5% glutaraldehyde, and sorensen's phosphate buffer, (Electron Microscopy Sciences), pH 7.4. The thread was then rinsed in a 6 inch trough containing 0.5X sorensen's phosphate buffer. The dwell time in each bath was 5 seconds. The thread was then air dried for 15 seconds and collected onto a stainless steel shaft.

EXAMPLE 3—BRAIDING COLLAGEN THREAD

A harness braiding machine (New England Butt Co., Providence, RI, USA) was used to braid collagen thread, both XL and non-XL, prepared in accordance with Examples 1 and 2, above.

The number of spools to be braided was varied, typically from 3 to 8. The type of thread was also varied as well (crosslinked, noncrosslinked, etc.). Care was taken to spool the thread onto a suitable carrier such that the thread unspooled freely and without snagging or excessive tension.

Braid tightness was varied by varying the gear ratio according to the instructions provided with the machine. Typically, the collagen thread to be braided was wound onto cylindrical stainless steel spools, approximately 0.8 inches in diameter. These spools were mounted onto the braiding carousel, and the thread gathered according to the instructions provided with the machine. In one run, a braid was composed of four strands: two threads of uncrosslinked (non-XL) collagen, and two threads of collagen which had been croslined (XL) in glutaraldehyde (supra). Equal lengths of thread were used on each spool to be braided. The load at break was greater than the sum of the load at break of the constituent threads.

EXAMPLE 4—PRODUCTION OF COLLAGEN YARN

Collagen thread produced in accordance with Examples 1 and 2 above has been plied into yarn, as other types of thread would be (e.g., cotton, polyester, etc.). Twisting methods and machinery used in producing this yarn are standard for the textile industry. Persons with ordinary skill in producing yarns from other types of thread may apply those same methods using the collagen thread of the present invention to achieve the desired result.

In one standard run, one uncrosslinked collagen thread and one crosslinked thread were each given a Z-twist at 6 twists per inch (tpi); then the two were twisted together in an S-twist with 4 tpi.

Yarns may be made of any desired nubmer of collagen threads, produced per Examples 1 and 2 above, in any combination of crosslinked and uncrosslinked. For example, 60 ply yarn has been made from uncrosslinked collagen threads of the present invention. In producing this 60 ply yarn, first 4 collagen threads were twisted together; then 3 of the resultant 4-ply strans were twisted together in the opposite direction; and finally 5 of the resultant 12-plly strans were twisted in the opposite direction.

EXAMPLE 5—KNITTING COLLAGEN THREAD AND YARN

Collagen threads and/or braided or plied yarns produced in accordancce with Examples 1-4 above, have been knitted into tubular or flat fabrics and meshes. The knitting methods and machinery used in the production of these articles are standard for the textile industry. Persons with ordinary skill in producing tubular or flat fabrics or meshes from other types of thread and/or yarn may apply those same methods using collagen thread and/or yarn to acheive the desired result.

Both a circular knitter: Lamb, Inc. (Agawam, Mass., U.S.A.) and a Warp Knitter: Karl Mayer Maschinen Fabrik (Germany) have been used to produce knitted articles. In one run, a tube of 3 mm inner diameter was knitted on the warp knitter from 2 ply yarn (1 non-XL and 1-XL collagen thread) prepared in accordance with Example 4 above with a double needle for using four ends and 1/0-½ (closed stich).

A wide range of diameters is possible, e.g., from about 4 mm to about 10 cm.

A circular knitter (Lamb Ing., Agawam, Mass., U.S.A.) was used in a warp knitting process wherein:

many ends came together and knit. This process produces circular knitted tubes which will not unravel when cut. Many parameters, including tension, type of stitch, number of ends, number of knitting bars, etc. can be varied.

EXAMPLE 6—PRODUCTION OF SUPPORT FOR BLOOD VESSEL EQUIVALENT 3 mm knitted tubes produced in accordance with Example 5 above have been used to produce collagen constructs. Such constructs were produced in accordance with Example 8 of copending U.S. application Ser. No. 07/505,678, except that the 3 mm knitted tube was used in place of the DACRON ® mesh.

It is understood that the examples and embodiments are for illustrative purposes only, and that various modifications or changes in light thereof that will be suggested to persons skilled in the art, are to be included in the spirit and purview of this application and the scope of the approved claims.

What is claimed is:

1. A method of making thread comprising collagen, the method comprising:
    (a) extruding a solution comprising collagen into a dehydrating agent, the dehydrating agent having a higher osmotic pressure than that of the collagen solution and a pH from about 5 to 9;
    (b) maintaining the dehydrating agent under conditions to enable the extruded collagen to form a thread.

2. The method of claim 1, further comprising rinsing the thread.

3. The method of claim 2, wherein the thread is rinsed in a buffer having a pH of about 7 to 8.

4. The method of claim 2, further comprising drying the thread before and after rinsing.

5. The method of claim 1, further comprising forming native banded fibrils in the thread.

6. The method of claim 1, further comprising crosslinking the collagen thread.

7. The method of claim 1, further comprising rinsing the thread, drying the rinsed thread, and crosslinking the dried thread.

8. The method of claim 1, wherein the dehydrating agent comprises a water soluble polymer.

9. The method of claim 8, wherein the dehydrating agent comprises at least one of polyethylene glycol and dextran.

10. The method of claim 9, wherein the dehydrating agent further comprises phosphate buffer.

11. The method of claim 1, wherein the collagen solution is at a concentration of about 2 to 10 mg/ml.

12. A method of making thread comprising collagen, the method comprising:
    (a) extruding a solution comprising collagen into a dehydrating agent having a higher osmotic pressure than that of the collagen solution and a pH from about 5 to 10;
    (b) maintaining the dehydrating agent under conditions to enable collagen thread formation;
    (c) rinsing the thread formed in step (b) in an aqueous buffer; and
    (d) crosslinking the collagen thread.

* * * * *